US006400971B1

(12) United States Patent
Finarov et al.

(10) Patent No.: US 6,400,971 B1
(45) Date of Patent: Jun. 4, 2002

(54) OPTICAL DEVICE FOR NON-INVASIVE MEASUREMENT OF BLOOD-RELATED SIGNALS AND A FINGER HOLDER THEREFOR

(75) Inventors: Alexander Finarov; Yossie Kleinman; Ilya Fine, all of Rehovot (IL)

(73) Assignee: Orsense Ltd., Rehovot (IL)

( * ) Notice: Subject to any disclaimer, the term of this patent is extended or adjusted under 35 U.S.C. 154(b) by 0 days.

(21) Appl. No.: 09/416,360

(22) Filed: Oct. 12, 1999

(51) Int. Cl.[7] ................................................ A61B 5/00
(52) U.S. Cl. ........................................................ 600/310
(58) Field of Search ................................. 600/310, 316, 600/322, 323, 334, 335, 340, 344

(56) References Cited

U.S. PATENT DOCUMENTS

| | | |
|---|---|---|
| 4,437,470 A | 3/1984 | Prost |
| 5,131,391 A | 7/1992 | Sakai et al. ................. 128/633 |
| 5,638,818 A | 6/1997 | Diab et al. ............... 128/653.1 |
| 5,782,757 A | 7/1998 | Diab et al. .................. 600/323 |
| 5,827,181 A * | 10/1998 | Dias et al. .................. 600/322 |
| 5,833,602 A * | 11/1998 | Osemwota .................. 600/310 |
| 5,860,919 A | 1/1999 | Kiani-Azarbayjany ...... 600/322 |
| 6,115,621 A * | 9/2000 | Chin .......................... 600/323 |

FOREIGN PATENT DOCUMENTS

| | | | |
|---|---|---|---|
| DE | 196 29 342 C2 | 1/1998 | ............ A61B/5/14 |
| EP | 0 444 934 A1 | 9/1991 | |
| JP | 10-33512 | 2/1998 | ............ A61B/5/14 |
| WO | WO 98/04182 | 2/1998 | |
| WO | WO 98/43096 | 10/1998 | |
| WO | WO 99/63884 | 12/1999 | |

* cited by examiner

Primary Examiner—Eric F. Winakur
Assistant Examiner—Joseph A Cadugan
(74) Attorney, Agent, or Firm—Fitch, Even, Tabin & Flannery

(57) ABSTRACT

An optical measurement device is presented. The device is attachable to the patient's body and adapted for performing non-invasive measurements of blood-related signals. The device comprises a measurement unit for applying optical measurements to a first region on the patient's extreme organ, and an occlusion assembly for applying over-systolic pressure to a second region on the patient's body located upstream of the first location with respect to a normal blood flow direction. A substantially flexible, heating element is provided within the measurement unit, and is accommodated so as to engage at least a part of the first region for heating it to a desired temperature.

23 Claims, 2 Drawing Sheets

OPTICAL DEVICE FOR NON-INVASIVE MEASUREMENT OF BLOOD-RELATED SIGNALS AND A FINGER HOLDER THEREFOR

FIELD OF THE INVENTION

The present invention is in the field of non-invasive measurements of physiological parameters of patients, and relates to a device for measuring blood-related signals.

BACKGROUND OF THE INVENTION

Numerous techniques have been developed for the non-invasive measurement of blood-related signals, being aimed at determining various blood-related parameters such as blood oxygen saturation and the concentration of substances contained in the blood, e.g., glucose. These techniques typically utilize a measurement device or probe, which is designed to be attached to a patient's body (typically his finger), and includes an optical assembly for irradiating the finger with light and detecting its light response.

Most of the known devices are based on spectrometric techniques. According to these techniques, a tissue is irradiated with light of different wavelengths, and a photodetector detects light returned from the tissue. Analysis of the detected returned signal allows the determination of the required biological variable. The accuracy of the method depends on various conditions, some of which are associated with the detected signal and others with the irradiated tissue. This technique gives poor results due to a low signal-to-noise ratio, artifacts and the fact that the returned pulsatile signal might be very low.

Recently developed techniques propose various solutions directed towards overcoming the above drawbacks. U.S. Pat. No. 5,131,391 discloses a pulse oxymeter aimed at overcoming a problem associated with constriction of blood vessels that might occur during stress or invasive procedures such as surgery. To this end, the pulse oxymeter, in addition to a photodetector, has a warming device.

U.S. Pat. No. 5,638,818 discloses a measurement device having an improved optical probe designed so as to reduce noise in the course of measuring signals in a compressible tissue. The probe includes a base having an aperture for the finger to be inserted therein, which aperture leads to a chamber where a photodetector is placed in a manner to have no contact with the finger. A light source is affixed to the finger above the chamber. This design enables to maintain the optical path of transmitted light. A scattering medium is interposed between the light source and the finger so as to improve the signal-to-noise ratio. In a later patent of the same author (U.S. Pat. No. 5,782,757) a disposable optical probe and a reusable probe in the form of a padded clip-on bracket are disclosed. The probes are designed so as to fit comfortably onto a patient's fingertip.

WO 9843096 discloses a measurement device, where measurements are applied to a part of the body whose thickness is modulated harmonically by at least two pressure modulating frequencies. This part of the body is irradiated with at least two different wavelengths, where at least one of them lies in a range of optical absorption of the blood components to be determined.

JP 10033512 discloses a measurement device having a slot for a patient's finger to be inserted thereto. The walls of the slot are coated by an insulating material. A light source and a detector are accommodated at opposite sides of the slot so as to be at opposite sides of the finger.

DE 19629342 discloses a measurement device in the form of a holder for holding a patient's finger at its one side in a manner to apply a slight pressure thereto. The device analyzes light reflected from the finger.

The above devices deal with natural pulsatile signals. What is actually measured by these devices is an enhanced optical pulsatile signal. It is known that a regular optical pulsatile signal is typically 2–3% of the total transmission. The above devices are capable of obtaining the enhanced pulsatile signal that reach 8–10% of the total light transmission intensity. This enhancement of the natural pulsatile signal is a boundary of all conventional techniques of the kind specified A different technique is disclosed in a co-pending application PCT/IL 99/00331 assigned to the assignee of the present application, where the measured signals are not pulsatile. According to this technique, a state of blood cessation is created in a medium under measurement. This enables to significantly enhance the measured light response of the medium, as compared to that of the previously described techniques dealing with the pulsatile signals.

SUMMARY OF THE INVENTION

There is accordingly a need in the art to facilitate non-invasive measurement of significantly enhanced blood-related non-pulsatile signals, by providing a novel optical measurement device.

It is a major feature of the present invention to provide such a device that can be easily attached to the patient's organ and enable to create the blood cessation state within a measurement region.

The present invention takes advantage of the fact that measurements taken during the state of blood cessation allows for a significant increase of the blood-related signals, as compared to those taken during the state of normal blood flow. This concept is disclosed in a co-pending application PCT/IL 99/00331, assigned to the assignee of the present application. To create a state of blood cessation within a patient's organ, over-systolic pressure should be applied thereto. Measurements are taken at a location downstream of that where the over-systolic pressure was applied with respect to the direction of normal blood flow.

The main idea of the present invention is based on the fact that heating and optionally pressuring, effects significantly enhance the blood-related signals to be measured. The measurement device according to the invention includes a measurement unit and occlusion assembly, which are spaced-apart from each other along the patient's organ, and the measurement unit comprises a substantially flexible heating element. This element, on the one hand, enables to heat an area under measurements to a desired temperature, and, on the other hand, is capable of providing pressurization and comfortable fixation of the organ, and prevents its displacement relative to an illumination-detection assembly during measurement.

There is thus provided according to one aspect of the invention, an optical measurement device for attaching to the patient's body to perform non-invasive measurement of blood-related signals, the device comprising:

a measurement unit for attaching to the patient's extreme organ, the measurement unit comprising an illumination-detection assembly for illuminating a first region within said organ, detecting light response of the illuminated region and generating data representative thereof, wherein the measurement unit comprises a substantially flexible heating element engaging at least a part of said first region for heating it to a desired temperature;

an occlusion assembly for applying substantially over-systolic pressure to a second region on the patient's body located upstream of said first region with respect to a normal blood flow direction; and a control unit, which is coupled to the measurement unit for selectively actuating the measurements, analyzing data indicative of the detected light response and determining at least one desired parameter of the patient's blood, and is coupled to the occlusion assembly for selectively operating this assembly.

The occlusion assembly includes a cuff associated with a pneumatic drive for applying the over-systolic pressure. The cuff is either a ring mountable onto the patient's organ, or a band with Velcro-like fasteners.

The measurement unit may be in the form of a clip supporting the illumination-detection assembly and having the substantially flexible heating element attached to its inner surface. Alternatively, the measurement unit may comprise only this substantially flexible heating element that supports the illumination-detection assembly. To this end, the element is in the form of a cuff-like cushion to be wrapped around the organ within the region under measurements. This cuff-like cushion is associated with a pneumatic drive, constituting together a pressurizing assembly for supplying desired, substantially under-systolic (e.g., 10–50 mmHg) pressure. His pressurizing assembly is aimed at, on the one hand, adjusting the cuff-like cushion to a specific patient, and, on tie other hand, providing slightly pressurization of the patient's organ within the measurement area, thereby enhancing the measured signals.

Preferably, the desired temperature for heating the region under measurements is approximately 37°–38°. Heating can be either continuously or by applying short thermal pulses (e.g., electrical or light energy) to accelerate heating of the measurement region to the desired temperature.

The substantially flexible heating element may be in the form of a film made of a thermoconductive material, or of a non-conductive flexible material with a heater implemented therein. Alternatively, the substantially flexible heating element may be a two- or three-layer structure. If the two-layer structure is used, the first layer, which is in contact with the patient's organ, is made of an insulating, material, and the second layer is made of an electrically conductive (i.e., heating) material. If the three-layer structure is used, the first layer, which is in contact with the patient's organ, is made of an insulating material, the intermediate layer is made of a heating material, and the third layer is made of a dielectric material.

The illumination-detection assembly may be of any known kind. The assembly may be designed for detecting either light transmitted through the illuminated region or light scattered (reflected) therefrom.

Preferably, the patient's organ under measurements is his finger.

According to another aspect of the present invention, there is provided a finger holder to be used in a measurement device performing non-invasive measurement of blood-related signals, the finger holder comprising:

a measurement unit for attaching to the patient's extreme organ, the measurement unit comprising an illumination-detection assembly for illuminating a first region within said organ, detecting light response of the illuminated region and generating data representative thereof, wherein the measurement unit comprises a substantially flexible heating element engaging at least a part of said first region for heating it to a desired temperature;

an occlusion assembly for applying substantially over-systolic pressure to a second region on the patient's body located upstream of said first region with respect to a normal blood flow direction; and a control unit, which is coupled to the measurement unit for selectively actuating the measurements, analyzing data indicative of the detected light response and determining at least one desired parameter of the patient's blood, and is coupled to the occlusion assembly for selective operating this assembly

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF A PREFERRED EMBODIMENT

More specifically, the present invention is used with a patient's finger, and is therefore described below with respect to this application.

Figure 1:
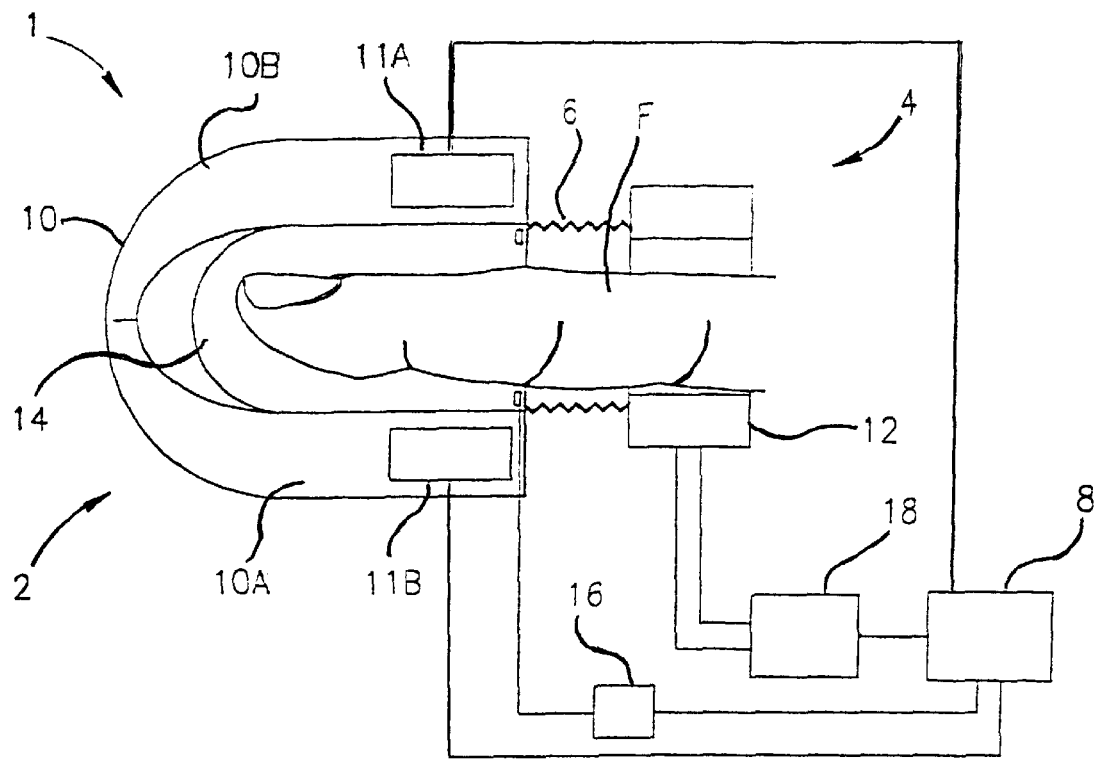
FIG. 1 illustrates a measurement device according to one embodiment of the invention, applied to the patient's finger.

Referring to FIG. 1, there is illustrated a measurement device 1, constructed according to one embodiment of the invention, being applied to a patient's finger F.

The device 1 comprises such main constructional parts as: a measurement unit 2 located at a first location on the finger F, an occlusion assembly 4 located at a second location on the finger F, a flexible connector 6 connecting the unit 2 and assembly 4, and a control unit 8 coupled to the unit 2 and assembly 4. The provision of the connector 6, which may be either flexible or rigid, is optional The measurement unit 2 includes a finger holder 10 in the form of a clip that comfortably secures the measurement unit onto the patient's finger, which is enclosed between opposite sides 10A and 10B of the clip 10. These opposite parts of the clip 10 also serve for holding an illumination unit 11A and a detection unit 11B, respectively. The construction and operation of such an illumination-detection assembly are known per se, and therefore need not be specifically described, except to note the following. The illumination unit 11A includes a suitable light source for illuminating a region of the finger with light of at least two different wavelengths, while the detection unit 11B includes a suitable sensor means for detecting light components transmitting through the illuminated region and generating data representative thereof. It should be noted that the illumination-detection assembly could be designed and accommodated in a manner to detect light reflected from the finger.

The data generated by the detection unit (measured data) are indicative of the time dependence of the intensity of the detected light for each wavelength. These data are transmitted to a processing utility of the control unit 8, which is operated by suitable software for analyzing the measured data and determining desired parameters of the patient's blood, for example the concentration of hemoglobin, glucose, cholesterol, etc. A calculation scheme suitable for the determination of these parameters is disclosed in the above-indicated co-pending application, and does not form part of the present invention.

Further provided in the measuring unit 2 is a cushion 14 attached to an inner surface of the clip 10 and coupled to a power source 16. The cushion 14 is made of a flexible material so as to provide comfortable fixation of the finger F and prevent its displacement relative to the illumination-detection assembly during measurements. By varying the thickness of the cushion 14, its flexibility can be desirably adjusted.

The cushion 14 is preferably made of a thermoconductive material having an electrical resistance suitable for heating the finger up to a desired temperature (e.g., 37°–38°) in response to the electric supply provided by the power source 16. Such a flexible and thermoconductive material may be rubber, silicone, PVC, thermoplasts, and other materials containing carbon or metal fillings.

The occlusion assembly 4 includes a flexible cuff 12 coupled to a pneumatic driver 18, which is, in turn, coupled to a corresponding utility of the control unit 8. The control unit selectively operates the driver 18 for applying, a constant, over-systolic pressure (e.g., 270–300 mmHg, but, generally, adjustable for each specific patient) to the second location of the finger F. It should be noted, although not specifically shown, that such a ring-like cuff 12 may be replaced by a band having Velcro-like fasteners.

The main operational principles of the device 1 are based on the following. It was found by the inventors, and disclosed in the above-indicated co-pending patent application, that that the optical characteristics of a blood flow containing medium (e.g., the patient's finger) start to change in time, when causing blood flow cessation In other words, once the blood flow cessation state is established, the optical characteristics start to change dramatically, such that they differ from those of a normal blood flow by about 25 to 45%, and sometimes even more than 60%. Hence, the accuracy (i.e., signal-to-noise ratio) of the optical measurements can be substantially improved by conducting at least two timely separated measurement sessions each including at least two measurements with different wavelengths of incident radiation. The light responses of the finger at these two sessions essentially differ from each other. At least one of the measurement sessions during which the measurement is effected should be chosen, either during temporary blood flow cessation, or daring the state of transitional blood flow. Alternatively, single blood current occlusion can be used, namely a single long occlusion measurement be taken and analyzed.

Thus, the patient's wears the device 1, and the control unit actuates the driver 18 to create the over-systolic pressure. Upon determining the establishment of the state of blood cessation, the control unit 8 operates the measurement unit 2 for carrying out one or more measurement sessions as described above, and the processing utility of the control unit 8 performs the data analysis.

Figures 2A, 2B:
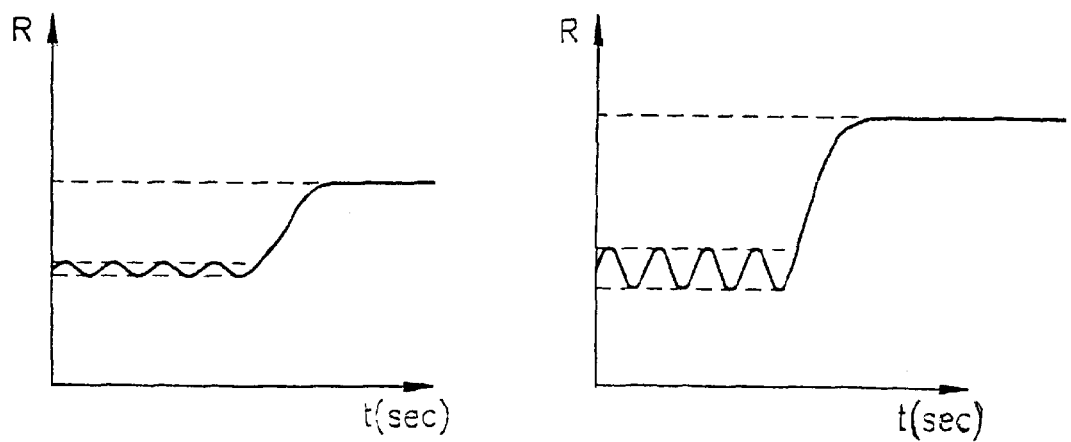
FIG. 2 graphically illustrates the main principles of occlusion-based measurements carried out by the device of FIG. 1.

FIG. 2 illustrates two graphs, $G_1$ and $G_2$ presenting experimental results corresponding to the time dependence of the blood-related signal R measured with the device 1 without and with the heating effect, respectively. As shown, the application of the device 1 creates a strong optical signal, approximately 30%–40% of the total transmission intensity, which is significantly increased by the heating effect.

Figure 3:
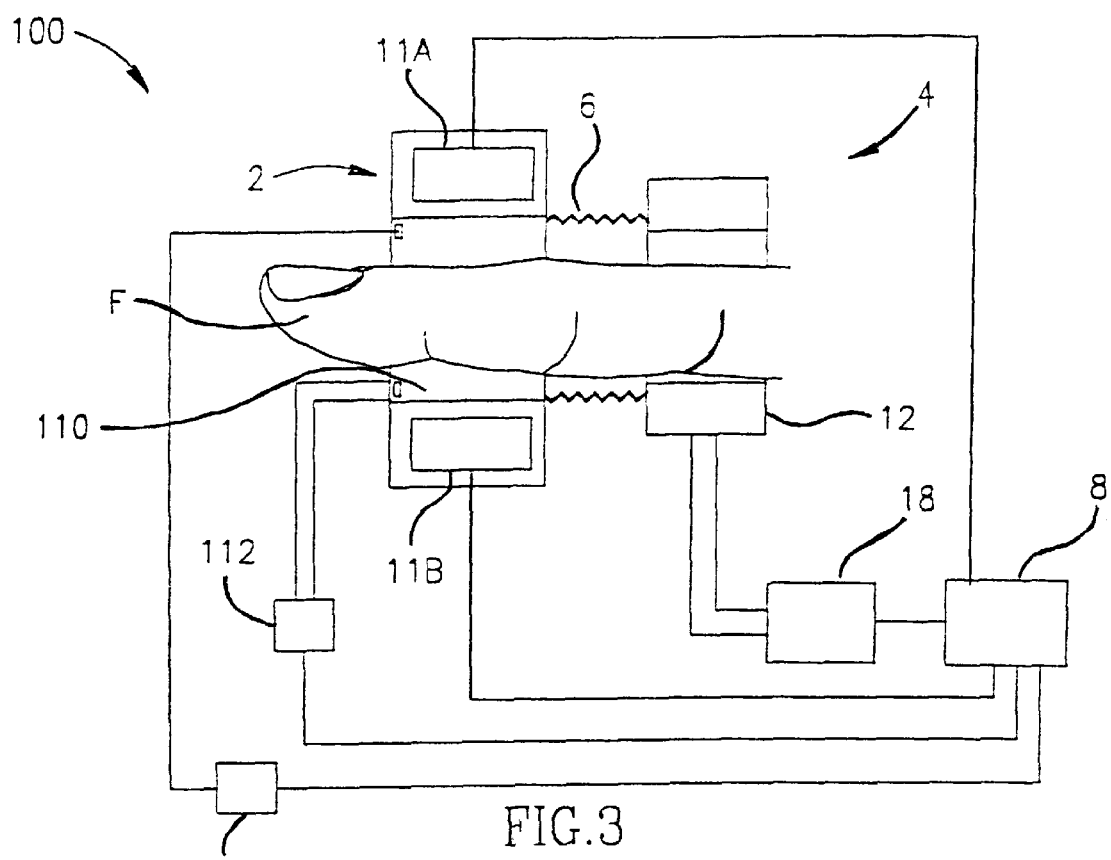
FIG. 3 illustrates another embodiment of the measurement device.

Reference is made to FIG. 3, illustrating a measurement device 100 constructed and operated according to another embodiment of the invention. To facilitate understanding, same reference numbers are used for identifying those components which are identical in the devices 1 and 100. The device 100 is constructed generally similar to the device 1, but has a finger holder designed somewhat differently, as compared to that of the device 1. Here, the combination of the clip 10 and cushion 14 is replaced by a flexible thermo-conductive cuff 110 coupled to a pneumatic drive 112 operated by the control unit 8. The cuff 110 and the pneumatic drive 112 constitute together a pressurizing assembly. It should be noted, although not specifically shown, that this pressurizing assembly may be mounted on the clip 10. In other words, the pressurizing assembly may replace only the cushion 14. Generally speaking, the finger holder may include both heating and pressurizing elements.

The cuff 110 supports the illumination and detection units 11A and 11B, and provides a required thermostabilization of electronic elements. To put the device 100 in the operation, a desired, substantially low pressure (e.g., 10–50 mmHg) is applied to the cuff 110, and suitable voltage is supplied thereto.

The cuff 110 is made from one of the above-listed flexible thermoconductive materials. These materials can be manufactured by any known suitable technique, such as press forming, injection molding, etc., and may have a wide range of electrical resistance enabling the operation with low voltage, for example, in the range 1–24V. This voltage supply is acceptable for medical devices. The low power supply of approximately 2–3 W allows for using batteries that enable the measurement device to be conveniently portable.

As indicated above, the cushions 14 (FIG. 1) or cuff 110 (FIG. 2) could be entirely manufactured from a thermoconductive, resistive material. It should, however, be noted that a non-conductive flexible element may be used with heating elements implanted therein. Alternatively, the cuff could be composed of two parts or layers. In other words, the cushion may have a two- or three-layer structure. In the case of the two-layer structure, the upper layer, which is contact with the finger, made of an insulating material such as silicone, rubber, polyethylene, etc., and the lower layer is made of a heating material, such as conductive silicone, rubber or other flexible, conductive materials. In the case of the three-layer structure, an intermediate layer is made of a heating flexible material such as electro-conductive silicone, rubber or flexible metal materials like NiCr films, wires, etc., and the lower layer is made of a dielectric materials, such as non-conductive silicone or rubber. Electrical contacts may either be installed in the flexible cushion or cuff during the manufacturing process, or be assembled in a separate process thereafter.

Figure 4:
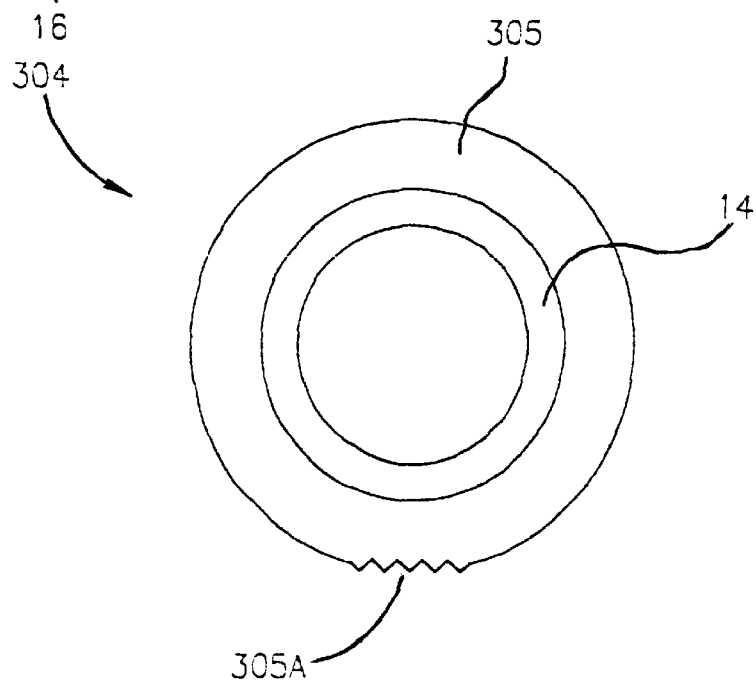
FIG. 4 illustrates yet another embodiment of the invention having a different construction of the measuring unit.

Turning now to FIG. 4, there is illustrated yet another embodiment of the invention aimed at avoiding the use of additional pneumatic means associated with the application of the under-systolic pressure, thereby rendering the measurement device even more portable. To this end, a measurement device 304 comprises the flexible heating cushion 14 put on the finger F, and a shrinkable ring or cap 305 having a spring portion 305A. The ring 305, after being heated by the voltage supply (not shown), presses the cushion 14 against the tension of the spring 305. When this pressure exceeds a maximum permissible tension of the spring, it tears off, thereby opening the electric circuit and stopping the heating.

The advantages of the present invention are thus self-evident. The measurement device according to the invention is portable and easy to operate. The device is inexpensive due to the use of low voltage supply. The provision of a holding member of adjustable diameter, i.e., the clip 10 and flexible cushion 14 (FIG. 1), cuff 110 (FIG. 3) or cushion 14 with the ring 305 (FIG. 4), enables the comfortable fitting of the finger's position. The heating effect enhances the measured signals, and the slight pressurization of the region under measurements enhances these signals even more.

Those skilled in the art will readily appreciate that various modifications and changes may be applied to the preferred embodiment of the invention as hereinbefore exemplified without departing from its scope defined in by the appended claims.

What is claimed is:

1. An optical measurement device for attaching to a patient's body to perform non-invasive measurement of blood-related signals, the device comprising:

a measurement unit adapted to be attached to one of the patient's extreme organs, the measurement unit being made up of an illumination-detection assembly for illuminating a first region within the extreme organ, detecting light response of the illuminated region, and generating data representative thereof, the measurement unit further including a substantially flexible heating element engaging at least part of the first region within the extreme organ for heating it to a desired temperature;

an occlusion assembly for applying over-systolic pressure to a second region on the patient's body located upstream of the first region with respect to a normal blood flow direction; and a control unit, which is coupled to the measurement unit for selectively actuating the measurements, analyzing data indicative of the detected light response and determining at least one desired parameter of the patient's blood, said control unit being further coupled to the occlusion assembly for selectively operating said occlusion assembly.

2. The device according to claim 1, wherein said desired temperature is approximately 37°–38°.

3. The device according to claim 1, wherein said substantially flexible heating element contains thermoconductive material.

4. The device according to claim 3, wherein said thermoconductive material is electrically conductive silicone.

5. The device according to claim 3, wherein said thermoconductive material is electrically conductive rubber.

6. The device according to claim 1, wherein said substantially flexible heating element is made of a non-conductive flexible material with a heater implemented therein.

7. The device according to claim 1, wherein said substantially flexible heating element is composed of two layers, the first layer, adapted to contact the patient's extreme organ, being made of an insulating material, and the second layer being made of a thermoconductive material.

8. The device according to claim 1, wherein said substantially flexible heating element is composed of three layers, the first layer adapted to contact the patient's extreme organ, being made of an insulating material, the intermediate layer being made of a heating material, and the third layer being made of a dielectric material.

9. The device according to claim 8, wherein said dielectric material is non-conductive silicone.

10. The device according to claim 8, wherein said dielectric material is non-conductive rubber.

11. The device according to claim 1, wherein said measurement unit comprises a pressurizing assembly for applying a desired, substantially under-systolic pressure to the patient's extreme organ in the vicinity of the first region.

12. The device according to claim 11, wherein said substantially flexible heating element is a cuff-like cushion associated with a pneumatic driver operated by the control unit for applying said desired, substantially under-systolic pressure.

13. The device according to claim 12, wherein said desired pressure is approximately 10–50 mmHg.

14. The device according to claim 1, wherein said occlusion assembly comprises a cushion cuff-like member for wrapping the second region of the patient's body, and a pneumatic driver coupled to said cushion cuff-like member so as to, when being operated by the control unit, apply said substantially over-systolic pressure to the second region of the patient's body.

15. The device according to claim 14, wherein said cushion cuff-like member is a ring mountable onto the patient's extreme organ.

16. The device according to claim 14, wherein said cushion cuff-like member is a bend having loop and hook fasteners so as to form a ring on the patient's extreme organ.

17. The device according to claim 1, wherein said measurement unit further comprises a clip-like member for supporting said illumination-detection assembly and holding the measurement unit on the patient's organ.

18. The device according to claim 1, wherein said over-systolic pressure is sufficient to create a state of substantial blood cessation with the second region of the patient's body.

19. The device according to claim 18, wherein said over-systolic pressure is about 270–300 mmHg.

20. The device according to claim 1, wherein the patient's extreme organ is a finger.

21. An optical measurement device for attaching to a patient's body to perform non-invasive measurement of blood-related signals, the device comprising:

a measurement unit including a finger holder and being adapted to be attached to a patient's finger, the measurement unit being made up of an illumination-detection assembly for illuminating a first region within the finger, detecting light response of the illuminated region, and generating data representative thereof, the measurement unit further including a substantially flexible heating element engaging at least a part of the first region within the finger for heating it to a desired temperature;

an occlusion assembly for applying over-systolic pressure to a second region on the patient's body located upstream of the first region with respect to a normal blood flow direction; and a control unit, which is coupled to the measurement unit for selectively actuating the measurements, analyzing data indicative of the detected light response and determining at least one desired parameter of the patient's blood, said control unit being further coupled to the occlusion assembly for selectively operating said occlusion assembly.

22. The device according to claim 21, wherein the measurement unit further comprises a pressurizing assembly for applying a desired, substantially under-systolic pressure to the patient's extreme organ in the vicinity of the first region within the extreme organ.

23. The device according to claim 22, wherein said substantially flexible heating element is a cuff-like cushion associated with a pneumatic driver operated by the control unit for applying said desired substantially under systolic pressure.

* * * * *